United States Patent [19]

Hsia et al.

[11] Patent Number: 4,897,245

[45] Date of Patent: Jan. 30, 1990

[54] CATALYTIC REACTOR SYSTEM FOR CONVERSION OF LIGHT OLEFIN TO HEAVIER HYDROCARBONS WITH SORPTION RECOVERY OF UNREACTED OLEFIN VAPOR

[75] Inventors: Chung-Hueng Hsia, Matawan; Hartley Owen, Belle Mead; Bernard S. Wright, East Windsor, all of N.J.

[73] Assignee: Mobil Oil Corp., New York, N.Y.

[21] Appl. No.: 678,954

[22] Filed: Dec. 6, 1984

Related U.S. Application Data

[63] Continuation-in-part of Ser. No. 576,179, Feb. 1, 1984, Pat. No. 4,511,747.

[51] Int. Cl.⁴ .................... C07C 7/00; C08F 4/00; C08F 6/04
[52] U.S. Cl. .................... 422/131; 422/134; 422/187; 422/211; 422/234; 422/235
[58] Field of Search ............ 585/313, 314, 315, 329, 585/415, 423, 531, 533; 422/131, 134, 187, 190, 211, 234, 235; 208/340, 342

[56] References Cited

U.S. PATENT DOCUMENTS

| | | | |
|---|---|---|---|
| 2,939,834 | 6/1960 | Evans | 208/101 |
| 3,542,892 | 3/1969 | Stoker et al. | 208/342 |
| 3,827,968 | 8/1974 | Givens et al. | 208/49 |
| 4,433,185 | 2/1984 | Tabak | 585/312 |
| 4,450,311 | 5/1984 | Wright et al. | 585/413 |
| 4,456,779 | 6/1984 | Owen et al. | 585/415 |
| 4,497,968 | 2/1985 | Wright et al. | 585/415 |
| 4,511,747 | 4/1985 | Wright et al. | 585/415 |

*Primary Examiner*—Kenneth M. Schor
*Attorney, Agent, or Firm*—Alexander J. McKillop; Charles J. Speciale; L. Gene Wise

[57] ABSTRACT

In the conversion of light olefins to heavier hydrocarbons, an improved recovery technique is provided for selectively removing unreacted light olefins from a catalytic reactor effluent. This system is useful in converting ethene-rich feedstocks to gasoline and/or distillate products, particularly in oligomerization processes employing shape selective siliceous catalysts such as ZSM-5 type zeolites. By recycling gasoline-range hydrocarbons as a sorbent liquid, unreacted $C_2{}^+$ components may be absorbed from reactor effluent vapor and returned for further contact with the catalyst.

9 Claims, 2 Drawing Sheets

CATALYTIC REACTOR SYSTEM FOR CONVERSION OF LIGHT OLEFIN TO HEAVIER HYDROCARBONS WITH SORPTION RECOVERY OF UNREACTED OLEFIN VAPOR

REFERENCE TO RELATED APPLICATIONS

This application is a continuation-in-part of copending U.S. patent application Ser. No. 576,179 filed 1 Feb. 1984, now U.S. Pat. No. 4,511,747 incorporated herein by reference.

FIELD OF THE INVENTION

This invention relates to processes and apparatus for converting light olefins to higher hydrocarbons, such as gasoline-range and/or distillate-range fuels. In particular, it relates to techniques for operating a catalytic reactor system with ethene-rich feedstock and a unique effluent fractionation recovery system.

BACKGROUND OF THE INVENTION

Improved catalytic hydrocarbon conversion processes have created interest in utilizing olefinic feedstocks, such as petroleum refinery streams rich in lower olefins, for producing $C_5+$ gasoline, diesel fuel, etc. In addition to the basic work derived from ZSM-5 type zeolite catalyst research, a number of discoveries have contributed to the development of a new industrial process, known as Mobil Olefins to Gasoline/Distillate ("MOGD"). This process has significance as a safe, environmentally acceptable technique for utilizing refinery streams that contain lower olefins, especially $C_2-C_5$ alkenes. This process may supplant conventional alkylation units. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over H—ZSM—5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products.

As a consequence of the relatively low reactivity of ethene (ethylene) with known zeolite oligomerization catalysts prior distillate-mode reactor systems designed to completely convert a large ethylenic component of feedstock would require much larger size than comparable reactor systems for converting other lower olefins. However, under severe conditions of temperature and pressure, 75% or more of ethene can be converted in a single pass. Recycle of a major amount of ethene gas from the reactor effluent can result in significant increases in equipment size especially recycle compressors.

Olefinic feedstocks may be obtained from various sources, including fossil fuel processing streams, such as gas separation units, cracking of $C_2+$ hydrocarbons, coal byproducts, alcohol or ether conversion, and various synthetic fuel processing streams. Cracking of ethane and conversion of effluent is disclosed in U.S. Pat. No. 4,100,218 and conversion of ethane to aromatics over Ga—ZSM—5 is disclosed in U.S. Pat. No. 4,350,835. Olefinic effluent from fluidized catalytic cracking of gas oil or the like is a valuable source of olefins suitable for exothermic conversion according to the present MOGD process. It has been found that an olefin-oligomerization process utilizing $C_2+$ olefinic feedstock can be operated to fractionate the effluent for ethene recovery. Accordingly, it is an object of the present invention to provide a unique effluent fractionation system for recovery of unreacted ethylene or the like for operation of an integrated MOGD type reactor system.

SUMMARY OF THE INVENTION

A novel system has been designed for recovering and recycling lower olefin in a continuous catalytic process. Apparatus and techniques are provided for converting light olefinic feedstock, especially gases comprising ethene, to heavier liquid hydrocarbon product. It is an object of this invention to effect conversion by a continuous technique for combining the feedstock stream with a liquid hydrocarbon diluent stream containing a major amount of gasoline range intermediate hydrocarbons including $C_5+$ olefins.

In a preferred embodiment, a continuous catalytic system is provided for converting ethene-rich olefinic feedstock to heavier hydrocarbons comprising reactor means for contacting the combined feedstock-gasoline stream at elevated temperature and pressure in a reaction zone with a shape selective medium pore zeolite oligomerization catalyst to convert at least a portion of olefinic components to heavier hydrocarbons, heat exchanger means for cooling oligomerization reaction effluent to condense at least a portion of said heavier hydrocarbons, means for separating the cooled and partially condensed effluent stream into an ethene-rich vapor stream and condensed liquid hydrocarbon stream, and fractionation means for distilling said condensed hydrocarbons to provide a gasoline stream, a distillate product stream and a light hydrocarbon vapor stream. The improved system comprises a means for contacting the ethene-rich vapor from the separating means and the light hydrocarbon vapor stream from the fractionation means under sorption pressure conditions with a cool liquid portion of the fractionated gasoline stream to sorb ethene into the liquid gasoline stream; and pump means for pressurizing and recycling the sorbed ethene and gasoline stream for combining with ethene-rich feedstock.

These and other objects and features of the novel MOGD system will be seen in the following description of the drawing.

DESCRIPTION OF PREFERRED EMBODIMENTS

An olefinic feedstock, such as $C_2-C_4$ olefins derived from alcohol dehydration or catalytic cracker (FCC) effluent, may be employed as a feedstock rich in ethene, propene, butenes, etc. for the process. Typically, the olefinic stock consists essentially of $C_2$-$C_6$ aliphatic hydrocarbons containing a major fraction of monoalkenes in the essential absence of dienes or other deleterious materials. The process may employ various volatile lower olefins as feedstock, with oligomerization of alpha-olefins being preferred for either gasoline or distillate production. Preferably the olefinic feedstream contains at least about 50 to 75 mole % $C_2$-$C_4$ alkenes.

Process conditions, catalysts and equipment suitable for use in the MOGD process are described in U.S. Pat. Nos. 3,960,978 (Givens et al), 4,021,502 (Plank et al), and 4,150,062 (Garwood et al). Hydrotreating and recycle of olefinic gasoline are disclosed in U.S. Pat. No. 4,211,640 (Garwood and Lee). Other pertinent disclosures include U.S. Pat. No. 4,227,992 (Garwood and Lee) and U.S. Pat. No. 4,450,311 (Wright et al.) relating to catalytic processes for converting olefins to gasoline/distillate. The above disclosures are incorporated herein by reference.

Catalysts

The catalytic reactions employed herein are conducted, preferably in the presence of medium pore shape selective silicaceous metal oxide crystalline catalysts, such as acid ZSM-5 type zeolites catalysts. These oligomerization catalyst include the crystalline aluminosilicate zeolites having a silica to alumina ratio of at least 12, a constraint index of about 1 to 12 and acid cracking activity of about 50–200. Representative of the ZSM-5 type zeolites are ZSM-5, ZSM-11, ZSM—12, ZSM—23, ZSM—35 and ZSM—38. ZSM—5 is disclosed and claimed in U.S. Pat. No. 3,702,886 and U.S. Pat. No. Re. 29,948; ZSM—11 is disclosed and claimed in U.S. Pat. No. 3,709,979. Also, see U.S. Pat. No. 3,832,449 for ZSM—12; U.S. Pat. No. 4,076,842 for ZSM—23; U.S. Pat. No. 4,016,245 for ZSM—35 and U.S. Pat. No. 4,046,839 for ZSM—38. The disclosures of these patents are incorporated herein by reference. A suitable shape selective medium pore catalyst for fixed bed is HZSM—5 zeolite with alumina binder in the form of cylindrical extrudates of about 1-5 mm. Other pentasil catalysts which may be used in one or more reactor stages include a variety of medium pore (~5 to 9Å) siliceous materials such as borosilicates, ferrosilicates, and/or aluminosilicates disclosed in U.S. Pat. Nos. 4,414,423, 4,417,086, 4,417,087 and 4,417,088, incorporated herein by reference. A preferred catalyst material for use herein is an extrudate (1-5 mm) comprising 65 weight % HZSM—5 and 35% alumina binder, having an acid cracking activity ($\alpha$) of about 160 to 200.

General Process Description

Figure 1:
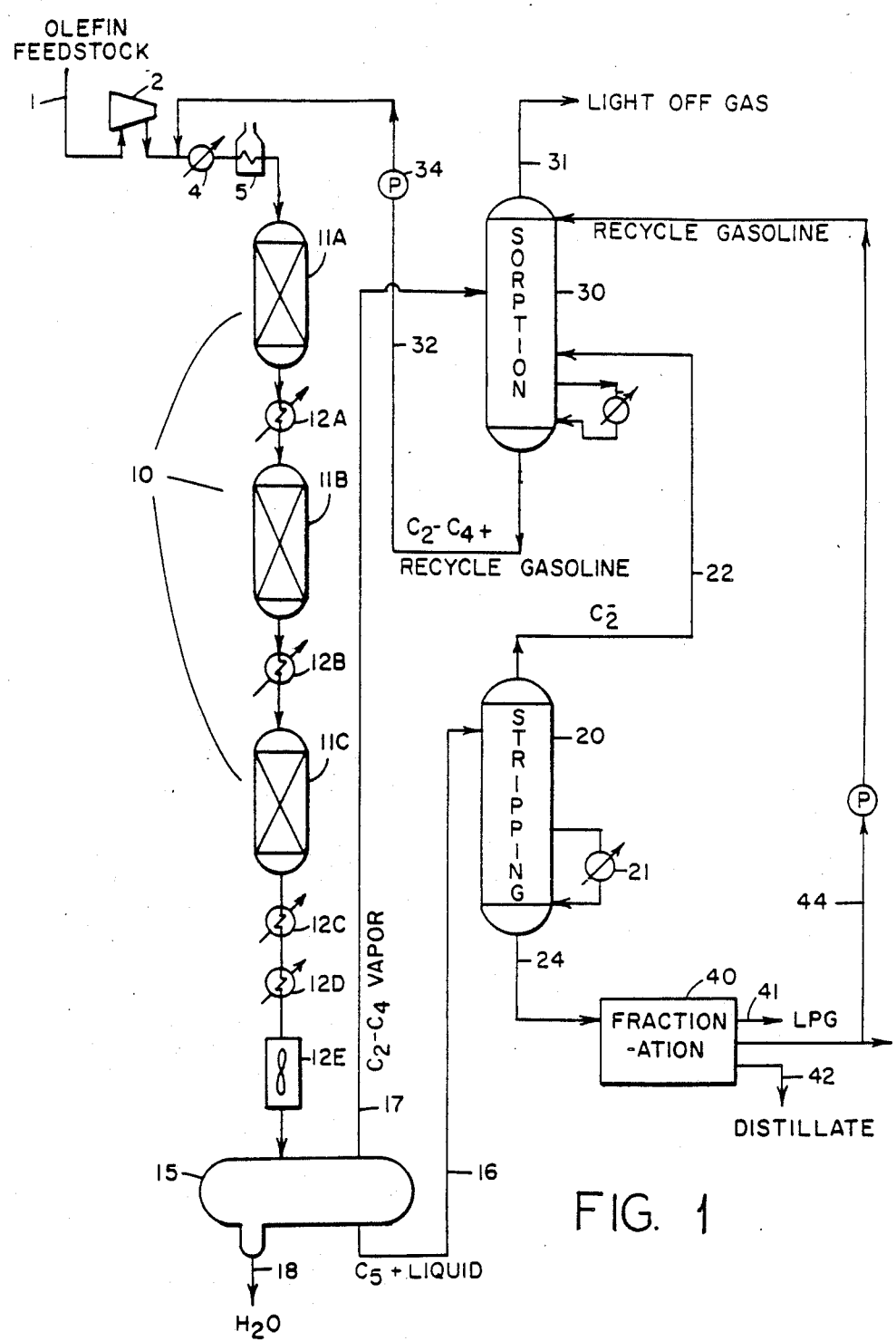
FIG. 1 is a process flow diagram showing relationships between the major unit operations.

Referring to FIG. 1 of the drawing, olefinic feedstock is supplied to the plant through fluid conduit 1 under steady stream conditions. This $C_2$+ feedstream is pressurized by compressor 2 and then sequentially heated by passing through process heat exchange unit 4 and furnace 5 to achieve the temperature for catalytic conversion in reactor system 10, including plural reactor vessels 11A, B, C, etc.

The reactor sub-system section shown consists of three downflow fixed bed, series reactors on line with heat exchanger cooling means 12 A, B, C, D, E between reactors and following the subsystem. The reactor configuration allows for any reactor to be in any position, A, B or C. The reactor in position A has the most aged catalyst and the reactor in position C has freshly regenerated catalyst. The cooled reactor effluent is first separated in a phase separator unit 15 to provide a condensed $C_5$+ hydrocarbon liquid stream 16 and an ethene-rich vapor stream 17 comprising $C_2$-$C_4$ aliphatic hydrocarbons, along with any other unreacted gaseous components which might be present in the feedstock, such as hydrogen, carbon oxides, methane, nitrogen or other inert gases. Extraneous water may be removed from the system through separator line 18.

Condensed hydrocarbon reactor effluent 16 separated from the effluent vapor is further fractionated. A stripping unit 20 which may be heated by exchanging a reactor effluent stream in reboiler 21, removes a significant fraction of dissolved light gases, including a minor amount of unreacted ethene. The $C_2$− stripped gases are passed through conduit 22 operatively connecting the stripper with a downstream sorption unit 30. Ethane and heavier hydrocarbons are removed from the recycle loop through stripper 20. This tower may be designed to lose as little ethylene as possible while maintaining a reasonable tower bottom temperature. High pressure favors the split between ethylene and ethane. Preferably the liquid stripper effluent 24 is debutanized in a fractionation subsystem 40 to provide a $C_4$− overhead stream, which is deethanized to provide LPG ($C_3$-$C_4$ alkane) product 41 and light offgas. The $C_5$+ debutanizer bottom stream is split in an atmospheric distillation tower to provide raw distillate product stream 42 and an olefinic gasoline stream 44 for recycle and/or recovery of a minor amount as raw gasoline product. Details of a suitable fractionation system and other process conditions are disclosed in U.S. Pat. No. 4,456,779 (Owen et al), incorporated herein by reference.

To recycle unconverted ethylene, recycle gasoline is used to selectively absorb it in the ethylene absorber 30. Ethylene is recovered from the vapor stream 17 leaving the reactor effluent separator and from the stripper overhead 22. The $H_2$, CO, $CO_2$ and $CH_4$ inerts which may enter with the feed are removed in the tower overhead via conduit 31 to prevent their build up in the system.

The gasoline sorbent is an aliphatic hydrocarbon mixture boiling in the normal gasoline range of about 50° to 165° C. (125° to 330° F.), with minor amounts of $C_4$-$C_5$ alkanes and alkenes. Preferably, the total gasoline sorbent stream to ethylene sorbate mole ratio is greater than about 4:1. The process may be operated with a mole ratio of about 0.2 moles to about 10 moles of gasoline per mole of $C_2$+ olefins in the feedstock.

The tower pressure and bottom temperature may be selected such that enough $CO_2$ leaves the system without carrying too much ethylene with it. Ethylene absorption efficiency can be improved if $CO_2$ is removed by an optional amine scrubber or the like (not shown) before entering the tower.

There is no need for a recycle compressor because all the recovered ethylene is dissolved in the recycle gasoline as a sorbate stream 32 and passed by pump 34 to the reactor. Advantageously, the liquid recycle stream is brought to process pressure before being heated to vaporize at least a portion of the olefinic components.

It is understood that the various process conditions are given for a continuous system operating at steady state, and that substantial variations in the process are possible within the inventive concept. In the detailed examples, metric units and parts by weight are employed unless otherwise specified.

The fractionation towers depicted in the drawing may employ a plate column in the primary tower and a packed column in the secondary tower, however, the fractionation equipment may also employ vapor-liquid contact means of various designs in each stage including packed beds of Raschig rings, saddles or other porous solids or low pressure drop valve trays (Glitsch grids). The number of theoretical stages will be determined by the feedstream composition, liquid:vapor (L/V) ratios, desired recovery and product purity.

Distillate Mode Reactor Operation

A typical distillate mode multi-zone reactor system employs inter-zone cooling, whereby the reaction exotherm can be carefully controlled to prevent excessive temperature above the normal moderate range of about 260° to 370° C.

Advantageously, the maximum temperature differential across any one reactor is about 30° C. ($\Delta T \sim 50°$ F.) and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with a fractionator stream to vaporize a liquid hydrocarbon distillation tower stream, such as the debutanizer reboiler. Optional heat exchangers may recover heat from the effluent stream prior to fractionation. Gasoline from the recycle conduit is pressurized by pump means and combined with feedstock, preferably at a mole ratio of about 2-3 moles per mole of olefin in the feedstock. It is preferred to operate in the distillate mode at elevated pressure of about 4200 to 7000 kPa (600–1000 psig), with a minimum olefin partial pressure of 1200 kPa at the reactor system inlet.

The reactor system contains multiple downflow adiabatic catalytic zones in each reactor vessel. The liquid hourly space velocity (based on total fresh feedstock) is about 1 LHSV. In the distillate mode the molar recycle ratio for gasoline is at least equimolar, based on total olefins in the fresh feedstock and recycle.

The preferred molar ratio olefinic gasoline to fresh feedstock olefin is at least 2:1. This will also assure adequate sorbent for the sorption unit.

Typical reactor conditions are set forth in the following tables.

TABLE I
REACTOR SYSTEM CONVERSION FEEDSTOCK AND YIELD

| Feedstock | | Yield on Olefin Converted | |
|---|---|---|---|
| Component | Wt % | Component | Wt % |
| Inerts | 5.00 | $CH_4$ | 0.10 |
| $CH_4$ | 2.00 | $C_2H_6$ | 3.90 |
| $C_2H_4$ | 81.20 | $C_3H_8$ | 4.00 |
| $C_2H_6$ | 0.62 | $IC_4H_{10}$ | 2.00 |
| $C_3H_6$ | 3.71 | $NC_4H_{10}$ | 2.00 |
| $C_3H_8$ | 0.20 | $IC_5H_{12}$ | 1.32 |
| $IC_4H_{10}$ | 0.25 | $NC_5H_{12}$ | 0.09 |
| $NC_4H_{10}$ | 0.45 | $C_5H_{10}$ | 2.99 |
| $C_4H_8$ | 0.12 | $C_6$–330° Gaso. | 39.60 |
| $IC_5H_{12}$ | 2.31 | 330° + Dist. | 44.00 |
| $NC_5H_{12}$ | 0.10 | | |
| $C_5H_{10}$ | 1.73 | | |
| $C_6+$ | 2.31 | | |

| Conversion on Feed to Reactor | |
|---|---|
| Olefins | Wt. % |
| $C_2$ | 75 |
| $C_3$ | 95 |
| $C_4$ | 85 |

TABLE II
REACTOR CONDITIONS

| | |
|---|---|
| Space Velocity, LHSV (Based on olefins fed to reactor) | 0.5 |
| Reactor A inlet pressure, psig | 900 |
| Minimum Olefin pp at reactor inlet, psia | 180 |
| Exothermic Heat of Reaction BTU/# olefins converted | 1040 |
| Rate of Heat Release | Uniformly over bed |
| Maximum Allowable $\Delta T$ in Reactor, °F. | 50 |
| Reactor Inlet Temperature SOC/EOC | 500/700° F. |
| Gasoline Recycle, Mol/Mol Olefin Feed | 2:1 |
| Coke on Catalyst, wt. % SOC | 0 |
| EOC | 30 |
| Cycle Length, Days | 30 |
| Catalyst | HZSM-5 1/16" Extrudate |

More than 90% of ethylene is recovered in the above example from the effluent.

Figure 2:
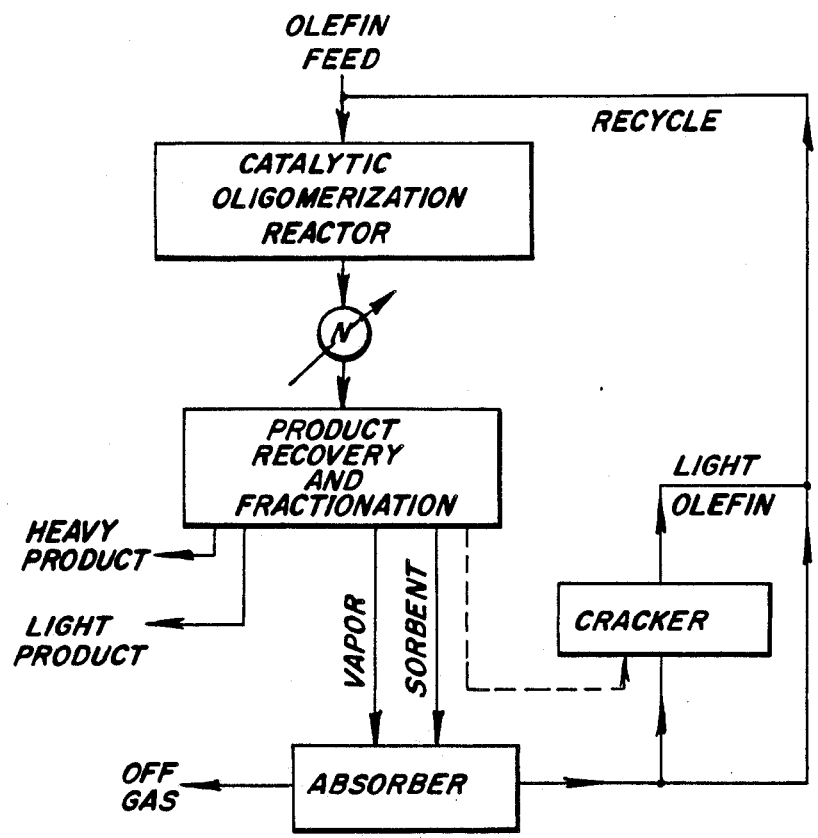
FIG. 2 is a schematic diagram of an alternative system.

The alternative embodiment shown in FIG. 2 employs the above described reactor, product recovery, fractionation and absorber units operatively connected for recycling at least a portion of unreacted olefin vapor from the effluent to the reactor unit. An optional cracking unit is provided to receive light and intermediate aliphatic hydrocarbons from the absorber. At least a portion of the $C_5+$ hydrocarbons may be cracked catalytically using zeolite catalysts of the type described or other cracking agents known to the art. The cracker effluent is rich in ethene and propene, which are converted in the main reactor with fresh olefin feed. Hot cracker effluent may be combined with diluent and olefin feed in a cascade flow arrangement. The cracking unit may also utilize a hydrocarbon stream from the product recovery and separation unit or other feed streams from outside the system loop, as desired.

While the invention has been described by specific examples and embodiments, there is no intent to limit the inventive concept except as set forth in the following claims.

What is claimed is:

1. A continuous system for converting ethene-rich olefinic feedstock to heavier liquid hydrocarbons comprising
   means for combining the feedstock stream with a liquid hydrocarbon stream containing a major amount of gasoline range hydrocarbons including $C_5+$ olefins;
   reactor means for contacting the combined feedstock-gasoline stream at elevated temperature and pressure in a reaction zone with shape selective medium pore zeolite oligomerization catalyst to convert a portion of the olefinic components to heavier hydrocarbons;
   heat exchange means for cooling oligomerization reaction effluent to condense at least a portion of said heavier hydrocarbons;
   means for separating the cooled and partially condensed effluent stream into an ethene-rich vapor stream and condensed liquid hydrocarbon stream;

means for fractionating said condensed hydrocarbons to provide a gasoline stream, a distillate product stream and a light hydrocarbon vapor stream containing unreacted ethene;

sorption means for contacting the ethene-rich vapor from the separation step and the light hydrocarbon vapor stream under sorption pressure conditions with a cooled liquid portion of the gasoline hydrocarbon to sorb ethene into the liquid gasoline stream; and means for recycling the sorbed ethene and gasoline stream for combining with an ethene-rich feedstock.

2. The system of claim 1 including means for recycling gasoline at a molar ratio of gasoline to fresh feedstock olefin of at least 2:1.

3. The system of claim 1 wherein the reactor means contains acid ZSM—5 type catalyst.

4. A continuous system for converting light olefinic feedstock comprising $C_2+$ monolefinic hydrocarbons to heavier hydrocarbons comprising reactor means for contacting the feedstock at elevated temperature and pressure in a reaction zone with zeolite catalyst to convert at least a portion of the olefinic components to heavier hydrocarbons;

heat exchange means for cooling reaction effluent to condense at least a portion of said heavier hydrocarbons;

means for separating the cooled and partially condensed effluent stream into a vapor stream comprising unreacted light olefin and a condensed liquid hydrocarbon stream;

means for fractionating said condensed liquid hydrocarbons to provide a recycle sorbent stream and at least one product hydrocarbon stream;

sorption means for contacting the vapor stream from the separation step and under sorption pressure conditions with cooled recycle sorbent to sorb said unreacted light olefin into the sorbent stream; and means for recycling the sorbent stream rich in olefin to said reactor means for further conversion with said olefinic feedstock.

5. The system of claim 4 comprising fractionation means for recovering an intermediate range hydrocarbon stream from condensed effluent and means for recycling at least a portion of said intermediate stream to the sorption means.

6. The system of claim 5 wherein the catalyst comprises an aluminosilicate zeolite having a silica to alumina mole ratio of at least 12 and a constraint index of about 1 to 12.

7. A catalytic reactor system for converting light olefinic feedstock to heavier hydrocarbons comprising:

catalytic reactor means comprising shape selective medium pore zeolite oligomerization catalyst for partially converting light olefins at elevated temperature and high process pressure to provide a hot reactor effluent stream comprising light olefinic hydrocarbon vapor and heavier hydrocarbons;

effluent cooling means for condensing at least a portion of said heavier hydrocarbons substantially at process pressure;

separating means for recovering a liquid heavy hydrocarbon stream and a light vapor stream rich in unconverted light olefinic components;

sorption means for contacting said light vapor stream from the separation means with a cool liquid sorbent stream under sorption conditions to recover said light olefinic components in a liquid sorbate stream;

stripper means for recovering a light gas stream from the condensed heavy hydrocarbon stream, said stripper means being operatively connected to pass recovered light gas to the sorption means for contact with liquid sorbent;

pump means operatively connected for pressurizing and recycling the liquid sorbate stream to the catalytic reactor means at process pressure;

fractionation means for recovering a distillate product stream and a gasoline liquid stream from the liquid heavy hydrocarbon stream from the separation means; and recycle means for passing at least a portion of the gasoline liquid stream to the sorption means as the sorbent stream.

8. In a continuous catalytic system for converting ethene-rich olefinic feedstock to heavier hydrocarbons comprising reactor means for contacting the feedstock stream at elevated temperature and pressure in a reaction zone with a shape selective medium pore zeolite oligomerization catalyst to convert a portion of olefinic components to heavier hydrocarbons, heat exchanger means for cooling oligomerization reaction effluent to condense at least a portion of said heavier hydrocarbons, means for separating the cooled and partially condensed effluent stream into an ethene-rich vapor stream and condensed liquid hydrocarbon stream, and fractionation means for distilling said condensed hydrocarbons to provide a gasoline stream, a distillate product stream and a light hydrocarbon vapor stream containing unreacted ethene; the improvement which comprises:

means for contacting the ethene-rich vapor from the separating means and the light hydrocarbon vapor stream from the fractionation means under sorption pressure conditions with a cool liquid portion of the fractionated gasoline stream to sorb ethene into the liquid gasoline stream; and pump means for pressurizing and recycling the sorbed ethene and gasoline stream for combining with ethene-rich feedstock.

9. The improved catalytic system of claim 8 further comprising means for recycling said gasoline stream at a molar ratio of gasoline to fresh feedstock olefin of at least 2:1, and wherein the reaction zone contains acid ZSM—5 type catalyst.

* * * * *